(12) United States Patent
Wendt et al.

(10) Patent No.: US 9,645,099 B2
(45) Date of Patent: May 9, 2017

(54) DEVICE FOR DETERMINING A COMPOSITION OF A LIQUID

(75) Inventors: Juergen Wendt, Stuttgart (DE); Dirk Schmidt, Kirchheim (DE); Stephan Schulteis, Gaggenau (DE); Werner Soergel, Pforzheim (DE); Thor Windbergs, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 143 days.

(21) Appl. No.: 14/354,259

(22) PCT Filed: Sep. 3, 2012

(86) PCT No.: PCT/EP2012/067097
§ 371 (c)(1),
(2), (4) Date: Mar. 5, 2015

(87) PCT Pub. No.: WO2013/064284
PCT Pub. Date: May 10, 2013

(65) Prior Publication Data
US 2015/0168312 A1      Jun. 18, 2015

(30) Foreign Application Priority Data

Oct. 31, 2011  (DE) .......................... 10 2011 085 490

(51) Int. Cl.
*G01N 22/00*  (2006.01)
*G01N 33/28*  (2006.01)
*G01N 33/22*  (2006.01)

(52) U.S. Cl.
CPC ............. *G01N 22/00* (2013.01); *G01N 33/22* (2013.01); *G01N 33/2835* (2013.01); *G01N 33/2852* (2013.01)

(58) Field of Classification Search
CPC .... G01N 22/00; G01N 33/22; G01N 33/2835; G01N 33/2852
See application file for complete search history.

(56) References Cited

U.S. PATENT DOCUMENTS

| 4,543,823 A | 10/1985 | Nagy et al. |
| 6,891,383 B2 * | 5/2005 | Nicholson .......... G01N 33/2888 324/643 |
| 2008/0143347 A1 | 6/2008 | Casey et al. |

(Continued)

FOREIGN PATENT DOCUMENTS

| DE | 10 2006 03488 | 4/2007 |
| DE | 10 2008 04438 | 6/2010 |
| EP | 0 069 969 | 1/1983 |

OTHER PUBLICATIONS

International Search Report, PCT International Application No. PCT/EP2012/067097, dated Dec. 19, 2012.

(Continued)

*Primary Examiner* — Hezron E Williams
*Assistant Examiner* — David Z Huang
(74) *Attorney, Agent, or Firm* — Gerard Messina

(57) ABSTRACT

A determining device for determining at least one component of a liquid, e.g., a fuel mixture, for use in motor vehicles, includes at least one sensor which has at least one connecting device for coupling microwave signals into the liquid and/or out of the liquid. The determining device is implemented as a hand-held measuring instrument.

7 Claims, 3 Drawing Sheets

(56) References Cited

U.S. PATENT DOCUMENTS

2008/0201084 A1* 8/2008 Lutnick .............. G01N 33/2829
  702/23

OTHER PUBLICATIONS

Santos, E.J.P. "Determination of ethanol content in gasoline: theory and experiment", Microwave and Optoelectronics Conference, 2003. IMOC 2003. Proceedings of the 2003 SBMO/IEEE MTT-S International Sep. 20-23, 2003, Piscataway, N.J., USA, IEEE (Sep. 20, 2003) vol. 1, pp. 349-353.

* cited by examiner

DEVICE FOR DETERMINING A COMPOSITION OF A LIQUID

BACKGROUND OF THE INVENTION

1. Field of the Invention

The present invention relates to a device for determining compositions of liquids, e.g., for use in motor vehicle.

2. Description of the Related Art

Devices and methods for determining compositions of liquids for use in motor vehicles are known from the related art. For example, fuel mixtures are being used increasingly in motor vehicles which, in addition to the actual petroleum fuels, may contain an admixture of ethanol and/or other alcohols. Usually parameters of the engine management of the motor vehicle are adapted to the composition of the fuel mixture. For this purpose, however, in many cases knowledge about the composition of the fuel mixture, especially an ethanol/fuel mixture ratio is required. Known measuring methods in this connection are the measurement of absorption, transmission or reflection of microwaves by the fuel mixture.

An example of a device equipped for this purpose is known from the published German patent application document DE 10 2008 044 383 A1. A method is described for determining a composition of a fuel mixture, in which a characteristic profile of a specific response to a microwave irradiation is recorded over a larger frequency range in order to ascertain the properties of the fuel mixture, and based on that, the composition of the fuel mixture is inferred. In particular, a measuring principle of a high-frequency sensor is described for determining the properties of fuel mixtures. An advantage of the method described in DE 10 2008 044 383 A1 is that, in particular, accuracy may be increased using larger frequency ranges so that, for example, alcohol-fuel mixtures, which also contain a water component and/or additives, may be characterized considerably more accurately than with conventional methods.

In the published German patent application document DE 10 2010 029 007, a device is described for determining a composition of a fuel mixture. The device includes at least one housing element, into which at least one inner conductor is introduced. In addition, the device has at least one connecting device for the coupling of microwave signals.

A device and a practical application of a measuring principle for a liquids tester, especially a fuel tester, which permits rapid analysis of the liquid for use in motor vehicles, especially of the fuel mixture, e.g., with regard to the following components: fossil content, ethanol content, water content and further contents, would be desirable. For example, the device and/or the measuring principle should be able to be used for what are referred to as blender pumps, at which, for example, a gas-station customer is able to preselect a fuel quality and/or the composition of the liquid, especially the fuel mixture. Furthermore, the device and/or the measuring principle should permit a diagnosis of the tank contents of flex fuel vehicles in a garage and/or for quality assurance of the fuel offered by gas stations, e.g., in third-world countries and/or emerging countries.

BRIEF SUMMARY OF THE INVENTION

Accordingly, a device is provided which is usable for determining a composition of a liquid, especially of a fuel mixture, for use in motor vehicles. The liquid is a liquid for use in motor vehicles, the device, for example, being able to be used in motor vehicles and/or outside of motor vehicles. For instance, the liquid may involve various types of mixtures, e.g., at least a biodiesel fuel and/or at least a urea-water solution and/or at least a coolant having antifreeze and/or at least an alcohol in aqueous solution. The fuel mixture may, in particular, be a fuel mixture for motor vehicles and/or for the operation of other fuel motors, e.g., a biodiesel fuel. In particular, the composition may be a mixture of at least two contents of at least two components of the liquid. It may, in particular, be a device for determining at least a content of at least one component in the liquid, especially in the fuel mixture. For example, the content of at least one component in the liquid, especially in the fuel mixture, may be a urea content and/or a water content, e.g., in the urea-water solution, and/or an antifreeze content, e.g., in the coolant, and/or an alcohol content, e.g., in the aqueous solution, and/or an ethanol content and/or a water content and/or a fossil content and/or a lead content and/or a sulfur content and/or an oxygen content and or a further content, for instance, in the fuel mixture, especially in the biodiesel fuel. For example, the content may be a percentage, e.g., a volume fraction and/or a mass fraction, and/or an absolute content, especially a volume and/or a mass, and/or a molar fraction. In general, the component may be a constituent of the liquid, especially of the fuel mixture, e.g., a constituent selected from the group made up of water, ethanol, oxygenates as well as possibly one or more other components.

Under the composition of the liquid, especially of the fuel mixture, may be understood, for example, to be the content of the at least one component in the liquid, especially in the fuel mixture. Over and above that, however, also understood under the term composition may be a temperature of the liquid, especially of the fuel mixture, and/or a mixture ratio and/or a mixture property, for example, a stratification of the liquid, especially of the fuel mixture, e.g., the presence of an inhomogeneous liquid, especially of an inhomogeneous fuel mixture in a tank, for instance.

The device has at least one sensor. In general, the sensor may be a device which preferably is usable to determine a composition of a liquid, especially of a fuel mixture. For example, the sensor may be a device as known from the related art, e.g., from DE 10 2010 029 007 and/or DE 10 2008 044 383 A1.

The sensor has at least one connecting device for coupling microwave signals into the liquid, especially into the fuel mixture, and/or out of the liquid, especially out of the fuel mixture. In particular, the connecting device may be a device which makes it possible to couple microwave signals into or out of the liquid, especially into or out of the fuel mixture, for example, to couple in or couple out simultaneously and/or to couple in and couple out in succession, preferably in any sequence, especially controllable by at least one user and/or at least one controller. The connecting device may include at least one transceiver coupler and/or at least one selector switch, especially for switching between the coupling of microwave signals into the liquid, particularly into the fuel mixture, and the coupling of microwave signals 116 into a calibration reference (Cal-Reference), and/or at least one HF peripheral, e.g., at least one microwave generator and/or at least one microwave transmitter and/or at least one microwave receiver and/or at least one microwave mixer and/or at least one amplifier and/or at least one attenuator and/or at least one microwave coupler and/or at least one HF-ASIC.

For example, the microwave signals may involve microwave radiation, especially continuous microwave radiation and/or microwave radiation varying in frequency stepwise and/or microwave pulses. The microwave signals may involve microwave radiation of at least one, preferably several frequencies. The amplitude and/or the phase of the microwave signals and/or the amplitudes and/or the phases of the components of the microwave signals having different frequency may, for example, be regulated, preferably independently of each other. For instance, the microwave signal may also be microwave radiation having a wide frequency spectrum. In principle, under the term microwave signals may be understood to be at least an electromagnetic high-frequency signal which preferably lies in a frequency range above 100 MHz or even 300 MHz, e.g., in a frequency range between 300 MHz and 300 GHz, in particular, between 300 MHz and 20 GHz, preferably between 500 MHz and 10 GHz and especially preferred, in the range of 0.5 and 8.5 GHz. Preferably, microwave signals are able to be coupled in over a frequency range, that is, a bandwidth. For example, microwave signals having at least two microwave frequencies may be coupled in. For instance, these microwave frequencies may be coupled in in succession and/or simultaneously. Preferably, the microwave frequencies cover a bandwidth of at least 100 MHz. For instance, this frequency range may be covered by the at least two microwave frequencies continuously or perhaps in regular or irregular steps. It is particularly preferred if the microwave signals coupled in include an ultra-wide-band microwave radiation. An ultra-wide-band (UWB) microwave radiation may be understood to be a microwave radiation in the sense of the definition above, which is able to use an extremely large frequency range, preferably with a bandwidth of at least 500 MHz.

In particular, the expression "into the liquid" may be understood to be a direction of a wave vector, preferably a direction of propagation, of the microwave signals, which points from a microwave transmitter toward the liquid, especially toward the fuel mixture. In this context, the microwave may preferably be conducted through a line up to at least one measuring area which preferably contains the liquid, particularly the fuel. The expression "out of the liquid" may in particular be understood to be a propagation of microwaves, preferably at least one wave vector of the microwaves pointing from the liquid, especially from the fuel mixture, toward a microwave receiver, particularly after at least one interaction, e.g., at least one reflection and/or at least one absorption and/or at least one refraction and/or at least one diffraction, with the liquid, especially with the fuel mixture.

The device is implemented as a hand-held measuring instrument. In this case, a hand-held measuring instrument may be understood to be a device which is connectable in extremely reversible manner to another device, e.g., a fuel tank and/or a fuel pump, e.g., a blender pump, and/or a fuel can. In this context, "reversibly connectable" may be understood to mean that a connection is able to be produced and/or released quickly by a user, for example, preferably without the use of tools and/or without damage. In particular, the hand-held measuring instrument may be understood to be a device which is able to be carried along, preferably independently, by a person, e.g. a user, on the basis of physical strength, for instance. In particular, the hand-held measuring instrument may have a total volume which does not exceed 10,000 $cm^3$, and which preferably does not exceed 1000 $cm^3$. In particular, the hand-held measuring instrument may have a weight which does not exceed 10 kg, e.g., does not exceed 5 kg, preferably does not exceed 2 kg. The user may be one skilled in the art, e.g., a vehicle mechanic and/or a qualified service-station employee, preferably any user. The hand-held measuring instrument is preferably mobile, e.g., portable by the user and/or user-friendly to operate. For example, the hand-held measuring instrument, especially the device, may be designed ergonomically, e.g., to be manipulable and/or comfortable for the user; for example, the device may have at least one carrying handle and/or at least one protective device, especially for protecting the health of the user. Furthermore, for instance, the device may also be made as light and compact as possible in order, for instance, to improve portability and/or manipulability and/or user-friendliness for the user.

In addition, the device may have at least one indicating unit and/or operating unit, preferably connectable, especially reversibly connectable, to the sensor, particularly for display of the composition and/or a case of a fault. In principle, the indicating unit and/or operating unit may also be connected irreversibly to the sensor. For example, "connectable" may be understood to be a possibility, according to which, for instance, a user is able to connect the sensor to the indicating unit and/or operating unit, e.g., by at least one plug-in connection and/or at least one screw connection and/or at least one Velcro-closure connection and/or at least one zip fastener and/or at least one button connection and/or at least one click connection. In this context, "reversibly connectable" may be understood to be a connection which may be produced and or released by the user, preferably with or without the use of tools. For instance, an irreversible connection may be understood to be a bonded connection and/or a welded connection. The indicating unit and/or the operating unit may also be implemented partially or completely separate from the sensor, and/or be ready-to-use. In this context, the indicating unit and/or operating unit and/or the sensor may be connected via electromagnetic waves, for example; in particular, an exchange of information may be possible between the indicating unit and/or operating unit and/or the sensor, particularly without mechanical connection of these components, e.g., by a connection via radio waves and/or Bluetooth. For example, the indicating unit and/or the operating unit and/or the sensor may also be coupled by a cable connection, e.g., by a network cable and/or an internet connection and/or another cable connection. For instance, the indicating unit may be understood to be a component of the device which displays the content of the component of the liquid, especially of the fuel mixture, and/or the composition of the liquid, especially of the fuel mixture, and/or a case of a fault and/or operating information and/or an instruction for the repair of a fault and/or a temperature of at least one part of the liquid, especially of the fuel mixture, and/or a state of charge of at least one battery and/or of at least one storage battery and/or the presence of at least one coupling and/or at least one connection between the sensor and/or the indicating unit and/or the operating unit and/or the state of a memory and/or a menu and/or other properties of the device. In general, the operating unit may be a component of the device, by which an operating person can have influence on the device, in particular, is able to operate it. In particular, the operating unit may be used for operator control by the user, e.g., as at least one man-machine interface. For instance, the operating unit may include at least one pushbutton and/or at least one touchpad and/or at least one touchscreen and/or at least one keyboard and/or at least one mouse and/or at least one operating knob and/or at least one speech control and/or at least one rotary knob and/or at least one rotary wheel and/or at least one key, e.g., for switching on, and/or at least one coin slot, e.g., for use at a gas station. In addition, the device may include at least one battery and/or at least one storage battery and/or at least one power supply cable, especially for the supply with electric voltage and/or electric current.

The indicating unit and/or the operating unit may include at least one display. In principle, as an alternative or additionally, the indicating unit and/or the operating unit may, for example, output and/or receive and/or process at least acoustical and/or haptic and/or visual and/or graphical and/or olfactory information. For example, the indicating unit and/or operating unit may include at least one segmented display, e.g., at least one 7-segment display, and/or at least one light-emitting diode and/or at least one touchscreen and/or at least one screen display and/or at least one microphone and/or at least one loudspeaker and/or at least one warning tone.

The device, particularly the indicating unit and/or operating unit, may include at least one data-processing device, especially at least one microcontroller and/or at least one drive circuit. The data-processing device and/or the microcontroller may, for example, include at least one evaluation software, particularly for evaluating the measuring results and/or for the operating control by the user of the sensor and/or the device. In general, the data-processing device may be a device which is set up to collect information from the indicating unit and/or the operating unit and/or the sensor and/or another component of the device, and/or to transmit information to them and/or to perform at least one computing operation. For instance, the data-processing device may be a computer and/or a controller, e.g., a microcontroller. Preferably, the microcontroller may be a computer which is designed to be as small as possible and/or is adapted especially to the device. For instance, the data-processing device may include at least one memory, e.g., for storing a number of compositions of the liquid, especially of the fuel mixture, and/or for storing at least a content of at least one component in a liquid, particularly in a fuel mixture, and/or for storing user data and/or for storing a time and/or for storing a temperature reading and/or an air pressure and/or a liquid temperature, especially a fuel-mixture temperature, and/or an outside temperature and/or for storing properties of a vehicle and/or of an engine. For example, the data-processing device may include at least one interface to at least one further device, e.g., at least one external unit, for instance, at least one USB interface and/or at least one serial interface, preferably for connection to at least one personal computer (PC) and/or to at least one data logger.

The device, particularly the sensor, preferably may have at least one housing. In particular, a housing may be understood to be a component of the device and/or of the sensor which protects one or more components of the device, including, e.g., the sensor and/or the indicating unit and/or the operating unit and/or the connecting device, for example, against environmental influences, e.g., against water and/or fuel and/or against the fuel mixture and/or against the liquid and/or against at least one component of the liquid.

Furthermore, for example, the housing may promote portability and/or user-friendliness and/or aesthetics and/or support of the device according to the present invention and/or of the sensor.

The at least one measuring area may be accommodated in the housing. A measuring area may be understood to be a component of the device, especially of the sensor, which is set up to receive a sample, e.g. a sample volume, of the liquid, especially of the fuel mixture. For instance, the measuring area may be a tank which has at least one, preferably two openings, e.g. for filling and/or discharging the liquid, especially the fuel mixture, and/or the sample and/or the sample volume. Preferably the liquid, especially the fuel mixture, may be introducible into the measuring area. The connecting device may be disposed at least partially in the measuring area. In principle, the housing may also at least partially involve at least one hose section and/or at least one pipe section. For example, the housing may have at least one flow-pipe section. In particular, the housing may be multipart.

The housing may be made at least partially of at least one plastic suitable for fuel and/or a plastic impervious to fuel. In particular, a plastic suitable for fuel and/or a plastic impervious to fuel may be understood to be a plastic which cannot be damaged by contact with fuel and/or fuel mixture and/or the liquid. In particular, it may be a plastic which leaves no constituents of the plastic in the liquid, especially in the fuel mixture, and/or absorbs no and/or allows no constituents of the liquid, especially of the fuel mixture, to pass through.

For example, the measuring area may be traversable by the liquid, especially the fuel mixture, and/or a sample of the liquid, especially of the fuel mixture. In this context, traversable may be understood to mean that the measuring area preferably includes at least one inlet and/or at least one outlet, a flow being able to develop from the inlet to the outlet which is able to be maintained during the filling and/or during the determination and/or which is able to be interrupted for the determination.

The housing, especially the measuring area, may in particular have at least one electrically conductive housing element through which the liquid, e.g., the fuel mixture, preferably is able to flow. In particular, the housing element may be understood to be a component of the housing. The housing element may especially be a metallic housing element. In particular, the housing element may be a sleeve or a cup. The housing element may especially be cylindrical, and be introduced into the housing transversely to a direction of flow of the liquid, especially of the fuel mixture. However, other embodiments are also possible. Preferably, the housing element and/or the housing is/are produced from at least one fuel-resistant material, e.g., a fuel-resistant metal such as a high-grade steel, for example, or other metallic material. In particular, one preferred material may be high-grade steel of the type 1.4301.

At least one inner conductor may be introduced into the housing element. In this context, an inner conductor may be understood to be a metallic conductor which is able to conduct electrical signals. For example, the inner conductor may be wire-shaped or pin-shaped and preferably may be essentially straight. Preferably, the inner conductor may be in contact with the liquid, especially the fuel mixture, when it flows through the housing element. The inner conductor may be enclosed at least partially by the housing element.

Preferably, the housing element may surround the inner conductor coaxially. In particular, the housing element may surround the inner conductor coaxially in such a way that, for example, the inner conductor may be accommodated concentrically in the preferably cylindrical housing element, e.g., the cup. Preferably, this may mean that an axis of the inner conductor and an axis of the housing element, e.g., the cup, essentially coincide, in which case slight deviations may also be possible, e.g., deviations by not more than 1 to 2 mm and/or by not more than 5°.

For example, the connecting device may be implemented as an electrical connector (plug), preferably for coupling the microwave signals to the sensor, especially to the inner conductor. In this context, coupling of the microwave signals may be understood to be a coupling of the microwave signals into the sensor, especially into the inner conductor and/or the housing or housing parts, and/or a coupling of microwave signals out of the sensor, particularly out of the inner conductor and/or out of the housing or housing parts. As explained above, the housing element may in particular surround the inner conductor coaxially. This means that, as explained above, the inner conductor runs, at least sectionally, essentially along an axis of the housing element in the interior of the housing element. The housing element may have at least one cup at least partially surrounding the inner conductor. For example, the cup may be a container, illustratively, the cup may be a metallic cup which, for example, may have a round and/or polygonal cross-section. For instance, the axis of the cup may extend transversely to a direction of flow of the liquid, especially of the fuel mixture, through the device, especially through the sensor, e.g., transversely to an axis of a flow pipe. For example, the cup axis may extend essentially perpendicular, i.e., for instance, at an angle of 90° to 20°, preferably 90° to 50° and especially preferred 90° to 80° relative to a flow-pipe axis. The cup, preferably outside of the flow cross-section, may in particular have a closed cup bottom. The cup may then be described as a hollow cylinder closed at one end by the cup bottom. The cup may be connected electroconductively to the inner conductor, especially in the area of the cup bottom. For example, the inner conductor may extend into and/or be inserted into the cup bottom, e.g., if the inner conductor is implemented as a connector pin, and/or may be connected electroconductively to the cup bottom in some other way. "Electroconductively connected" may be understood, in particular, to be an electrical connection having an ohmic resistance of less than 10Ω, preferably less than 1Ω, especially preferred, less than 1μΩ.

The housing element, especially the cup, may, in particular, have a plurality of boreholes. In this context, a borehole may be understood in particular to be an opening through which fuel and/or the liquid, especially the fuel mixture is allowed to flow into the interior of the cup and/or the liquid, especially the fuel mixture, e.g., the fuel is allowed to flow out of the interior of the cup. Thus, the cup preferably has a plurality of boreholes. The boreholes preferably have a diameter which is smaller than the smallest wavelength of the coupled-in microwaves, especially less than 2 mm, preferably less than 1 mm. In this way, a coupling-out of microwaves, which develop between the inner conductor and the cup or the inner wall of the cup, may be avoided. For example, for E100, thus fuel, especially a fuel mixture, having a nominal ethanol content of 100%, given a frequency f=19 GHz, the wavelength, particularly because of the dispersive properties of the ethanol, is usually λ=7 mm. In general, the boreholes may have any cross-section. Around cross-sections are especially preferred. However, in principle, non-round cross-sections are also conceivable. A "diameter" in the case of non-round cross-sections, e.g., polygonal cross-sections, is to be understood, for instance, as an "equivalent diameter", e.g., a diameter of a circle having equal opening area.

The connecting device, preferably situated between the sensor head and/or a measuring head and the housing and/or a measuring device, may include at least the inner conductor. In principle, however, the inner conductor may also be separate from the connecting device. The connecting device may have at least one coaxial connector. The coaxial connector may include at least one contact for applying microwave signals to the connecting device, especially the inner conductor. In particular, a coaxial connector may be understood to be a connector which includes a conductor and/or is surrounded by a conductor that preferably serves as ground. For instance, the coaxial connector may be a male or a female connector which preferably is able to be connected to a female or male connector. In particular, the contact may be understood to be an electroconductive connection, as specified above. In principle, the connecting device may also have another connector and/or another plug-in connection. Especially preferred in this context are standardized plug-in connections. The connector and/or the plug-in connection and/or the coaxial connector may have at least one contact for applying microwave signals to the inner conductor, thus, for coupling microwave signals in and/or out. In the case of a coaxial connector, the contact may be surrounded by at least one shielding connector part. For example, SMA-RP plug-and-socket connectors may be used in this case. Alternatively or additionally, at least one permanent, i.e., non-detachable connection may also be possible, e.g., at least one soldered connection.

Furthermore, the housing may have at least one flow-pipe section through which the liquid, especially the fuel mixture, is able to flow in a direction of flow. The inner conductor and the housing element may be placed transversely, preferably essentially perpendicularly, i.e., with the deviation tolerances described above, relative to the direction of flow in the flow-pipe section.

For example, the device, especially the sensor, may include at least one plug-in cartridge and/or the inner conductor and/or the housing element as well as possibly further elements. For instance, the plug-in cartridge may encompass the cup described above as well as the inner conductor placed in the cup. The plug-in cartridge may be plugged into an accommodation of the flow-pipe section in the measuring area transversely to the direction of flow. Preferably, the boreholes in the cup are then each oriented so as to be assigned to the direction of flow, so that, for example, the liquid, especially the fuel mixture, is able to flow through the cup of the cartridge without diversion of the flow. For instance, the accommodation may include an expansion in the housing, e.g., having at least one receiving borehole into which the cartridge is able to be inserted transversely to the direction of flow. In this context, the insertable accommodation may be implemented reversibly or perhaps permanently. For example, after the cartridge has been inserted, the cartridge may be fixed in position in the accommodation, e.g., by a screw connection, caulking, clamping rings or other types of fixations. Furthermore, the plug-in cartridge may be sealed off with respect to the flow-pipe section, especially with the aid of at least one sealing element. For instance, one, two, four or more O-rings may be provided for this purpose. For example, the connecting device described above may be disposed, e.g., on an end face of the cartridge outside of the flow-pipe section, so that, illustratively, the flow-pipe section and/or the cartridge, e.g., the plug-in cartridge, and/or the connecting device, e.g., the plug-in connection, form a T-configuration. Furthermore, the flow-pipe section may, for example, have two or more connections, e.g., at least one feed connection and/or at least one drainage connection. These connections may be standardized, e.g., may be implemented in the form of inexpensive and/or standardized connections, for example, according to the SAE standard.

The device, particularly the sensor, may include a flow-pipe section through which the liquid, especially the fuel mixture, is able to flow. The housing element and the inner conductor may be accommodated in the measuring area. A flow-pipe cross-section in the measuring area may be expanded compared to a flow-pipe cross-section outside of the measuring area. For instance, the flow-pipe section may be an essentially linear or straight flow-pipe section, e.g., having two hydraulic connections. This means that the measuring area is traversed by flow in a larger cross-section than other areas of the device, especially of the sensor, e.g., areas of the flow pipe outside of the measuring area. In other words, the flow in the measuring area may be expanded. In particular, the expansion may be accomplished by providing within the measuring area, one, two or more shells, e.g., as component of the cartridge, which ensure the expansion in the measuring area, e.g., for a continuous expansion, thus, an expansion having an essentially linear progression. For example, the expansion shells are able to prevent dead volume in the transition between the flow-pipe cross-section and the measuring area, e.g., at the transition between the flow-pipe section and the plug-in cartridge. For example, the shells may be ring-shaped and may likewise be accommodated concentrically about the inner conductor in the plug-in cartridge, for instance. The shells may be produced, for example, of a plastic material, e.g., a fuel-resistant plastic material, illustratively, a fluorinated polyethylene, preferably like the housing, as well.

The sensor may include at least one sensor head. For example, the sensor head may be understood to be a component of the device which has at least partial contact with the liquid, especially with the fuel and/or the fuel mixture, during the determination. For instance, the sensor head may encompass the sensor at least partially, e.g., the hydraulic connections and/or parts of the housing of the sensor. The sensor head may preferably be disposed outside of a housing, however may also be surrounded completely or partially by a housing. Preferably, the sensor head is able to be taken off of the sensor and/or the device, e.g., for cleaning in order to remove contaminants from the liquid, especially from the fuel mixture, particularly by the user.

The sensor head may include at least one admission device for admitting the liquid, particularly the fuel mixture, to the device, especially the sensor, particularly at least one admission device selected from the group made up of a funnel device and an adapter, especially an adapter for the connection of a quick hose connector. In principle, the admission device may be any device which is capable of admitting the liquid, especially the fuel mixture, and/or a sample of the liquid, especially of the fuel mixture, and/or conducting it to the measuring area and/or to conduct and/or to discharge the liquid, especially the fuel mixture, out of the device. For example, the funnel device may be a device reversibly connectable to the device, e.g., to the sensor head and/or the sensor, preferably a funnel, particularly a conically shaped pipe. The adapter may preferably be a device, e.g., a connector, which is able to be connected, for example, to at least one hose and/or to at least one pipe. Furthermore, the admission device may include a pump, for instance, which is able to pump the liquid, especially the fuel mixture, into the device, particularly into the sensor, and/or out of the device, particularly out of the sensor. For example, the admission device may include a device which is able to produce an underpressure and/or an overpressure in such a way that liquid, especially fuel mixture, and/or a sample of the liquid, especially of the fuel mixture, is sucked into the sensor by an underpressure, and/or is pushed out of the sensor by the overpressure. The funnel device and/or the adapter may, in particular, be connected reversibly, but in principle also irreversibly, to the sensor head and/or the sensor.

The sensor and/or the sensor head and/or the device may be completely or partially immersible in the liquid, particularly the fuel mixture, especially in a tank containing the liquid, particularly the fuel mixture. The sensor and/or the sensor head and/or the device may be immersible in the liquid, especially in the fuel mixture, and/or in the tank in such a way that at least a portion of the liquid, especially of the fuel mixture, particularly a sample of the liquid, especially of the fuel mixture, may be removed and/or is able to get into the measuring area. The liquid, especially the fuel mixture, and/or the sample of the liquid, especially of the fuel mixture may arrive in the measuring area independently, for example, and/or may reach the measuring area due to the pump and/or the underpressure and/or the funnel and/or the funnel device and/or via the adapter. In principle, the tank may be any container in which the liquid, e.g., the fuel, especially the fuel mixture, may be located. For instance, it may be a tank of a motor vehicle and/or the tank of a gas pump and/or a gas pump and/or a tank of an oil tanker and/or the tank of a fuel truck and/or a fuel-oil tank and/or a fuel can and/or a body of water which is contaminated with liquid for use in motor vehicles, especially fuel and/or fuel mixture, e.g., an ocean and/or a river and/or a lake and/or a building after having been contaminated with a liquid for use in motor vehicles, especially a fuel and/or a fuel mixture.

The device, particularly the sensor, may include at least one temperature sensor. In principle, the temperature sensor may be a device which is equipped to detect a temperature, e.g., an outside temperature and/or a temperature of the liquid, especially of the fuel, and/or a temperature of the fuel mixture. For instance, the temperature sensor may be a thermometer. The temperature sensor may be a temperature-dependent resistor, for example.

For example, the device may be implemented completely or partially as a built-in unit, particularly for a pump, especially preferred for what is termed a blender pump. In this context, the built-in unit may be understood to be a device which makes it possible to at least partially integrate and/or install, especially permanently install, the device in at least one other device.

Depending on the need, the device of the present invention may preferably be operated as a built-in unit. For this, the device may be installed, preferably reversibly, completely or partially, e.g., the sensor, in another device. For example, the device may be installed completely or partially in a pump for pumping one or more liquids, e.g., what is referred to as a blender pump. In particular, the device of the present invention may be implemented completely or partially as a fuel-quality module, e.g., as a permanent fitting in the blender pump, preferably as a monitoring instrument for the fuel quality. For example, the device may include at least one interface and/or at least one fitting device, particularly at least one connection possibility, for instance, at least one aperture, e.g., having a thread, and/or at least one holder and/or at least one bar and/or at least one possibility for a screw connection and/or welding and/or bonding and/or riveting. The built-in unit may be designed to be integrated and/or installed permanently at least to some extent or reversibly in at least one other device, e.g., in the blender pump and/or in the motor vehicle. "Permanently integrated and/or installed" may be understood to mean that at least one tool must be used for the integration and/or the installation and/or a removal. The expression "reversibly integrated and/or installed" may be understood to mean, for example, that the built-in unit may be installed and/or removed and/or integrated as often as desired, especially without damaging the device, preferably also without the use of at least one tool. A blender pump may be understood to be a device which may be used for withdrawal and/or mixing of the liquid, especially the fuel mixture. For example, the blender pump may be implemented as a fuel pump, especially for the withdrawal and/or mixing of a fuel mixture preselected by the user, particularly with preselected composition of the fuel mixture or the liquid.

For instance, the sensor may be reversibly exchangeable, various types of sensors being able to be used, preferably in order to employ the device for various types of liquids like those listed above, for example. The expression "for various types of liquids" may mean, for example, that the sensor may be specialized for at least one liquid for use in the motor vehicle, e.g., with regard to wavelengths and/or intensities and/or filters and/or materials and/or dimensions used. The sensor may be selected from the group made up of: a biodiesel-fuel sensor; a urea/water solution sensor; an alcohol solution sensor; an antifreeze/coolant sensor. The exchange and/or the use of other sensors, e.g., for other liquids, especially for other fuel mixtures, may also be possible in principle. For example, the biodiesel-fuel sensor may be a sensor designed to determine an ethanol content and/or a water content and/or a fossil content and/or an oxygen content and/or a further content in a fuel mixture, especially in a biodiesel fuel. The urea/water solution sensor may be a sensor, for example, which is designed to determine a urea content and/or a water content, e.g., in the urea/water solution. The alcohol solution sensor, for instance, may be a sensor which is designed to determine an alcohol content, e.g., in the aqueous solution. The antifreeze/coolant sensor may, for instance, be a sensor which is designed to determine an antifreeze content, e.g., in the coolant. For example, the sensor may also be a combination of the sensors indicated, or one of the sensors indicated may, for instance, be combined with at least one other sensor. For example, the device may include one of the indicated sensors in a plurality.

In a further aspect of the present invention, a method is described for determining a composition of a liquid, especially of a fuel mixture, for use in motor vehicles. Microwave signals are coupled into the liquid, especially the fuel mixture, over a frequency range. Response signals are received utilizing the device. From a comparison of the coupled-in microwave signals, at least one characteristic value is determined as a function of the microwave frequency of the microwave signals coupled in. The composition of the liquid, especially of the fuel mixture, is inferred from the profile of the characteristic value over the microwave frequency. The device is operated by a user.

With the aid of the at least one user, the sensor is able to be acted upon by the liquid, especially the fuel mixture, particularly by dipping the sensor and/or the sensor head and/or the device into the liquid, particularly into the fuel mixture. In this context, for example, response signals may be reflected and/or transmitted signals. For example, the method described in DE 10 2008 044 383 A1, or alternatively, the method described in DE 10 2010 029 007 may be used for this purpose. In principle, however, other methods may be used as well.

The device described above and the method described above may have numerous advantages compared to known devices and methods. Thus, the present invention includes a hand-held measuring instrument, particularly for rapid analysis, e.g., of liquids for use in motor vehicles, especially present-day and future flex fuels and/or other fuel mixtures.

Further advantages, for example, are rapid and/or precise determination of the main components, e.g., the portions, in the liquid, especially in the fuel mixture, for instance, for diagnosis of a tank contents, especially for diagnosis of contents of the tank of flex fuel vehicles, for example, especially of flex fuel vehicles in the garage, e.g., for quality assurance of the fuel offered by service stations, especially in third-world countries and/or emerging countries, for example. The device may also be used, for example, after environmental catastrophes to determine, for instance, portions of fluids, intended for use in motor vehicles, present in bodies of water, especially fuel mixtures in bodies of water, and/or to contribute to a rapid analysis of the liquid for use in motor vehicles, e.g., the fuel, especially the fuel mixture, with regard to the components fossil content, ethanol content, water content and further contents, e.g., in the case of blender pumps.

Thus, for example, the device of the present invention may be used especially as an ethanol sensor and/or diagnostic unit for flex fuel vehicles.

DETAILED DESCRIPTION OF THE INVENTION

Figure 1:
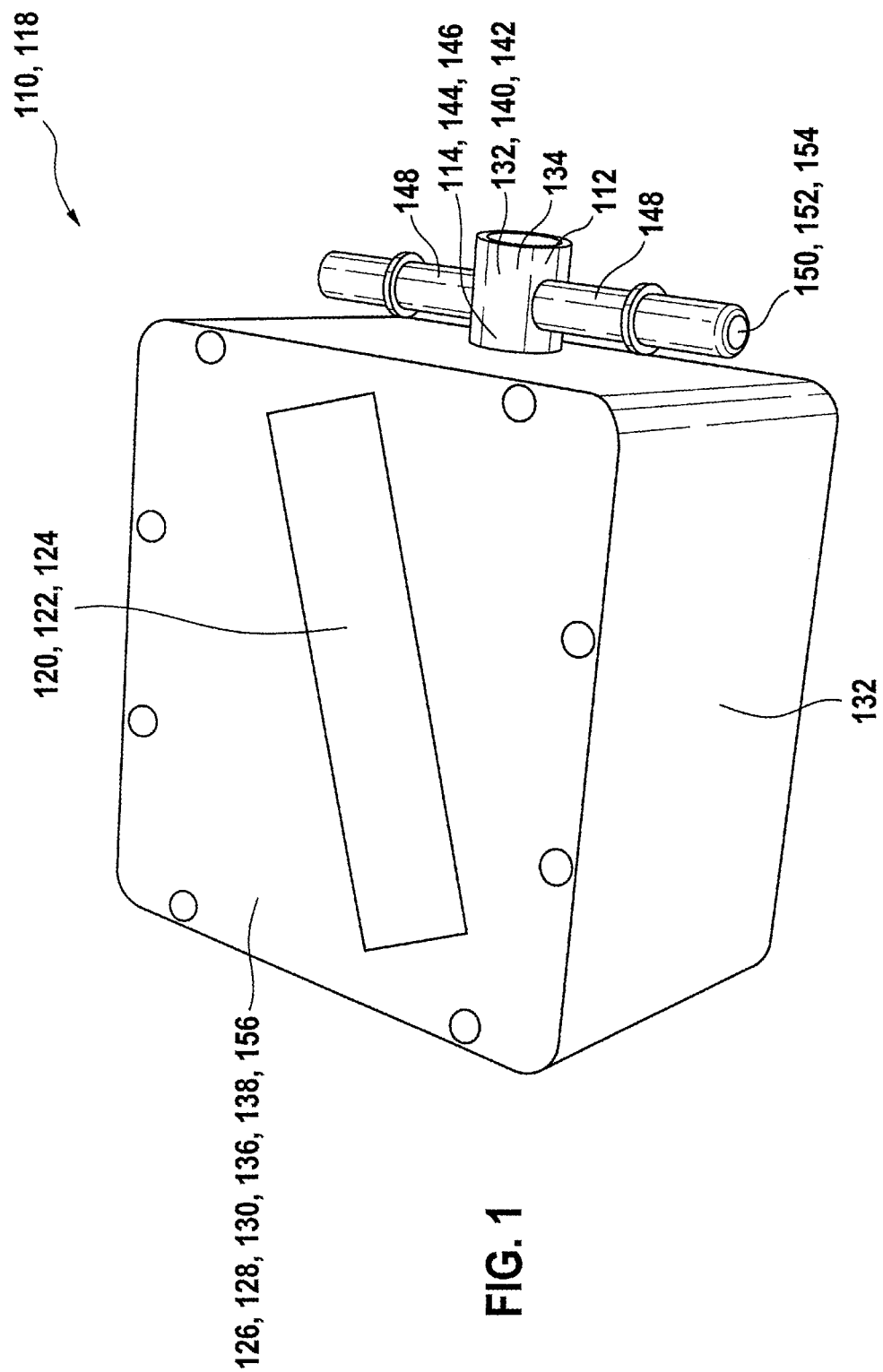
FIG. 1 shows a perspective view of an exemplary embodiment of a device according to the present invention for determining a composition of a liquid, especially of a fuel mixture, for use in motor vehicles.
Figure 2:
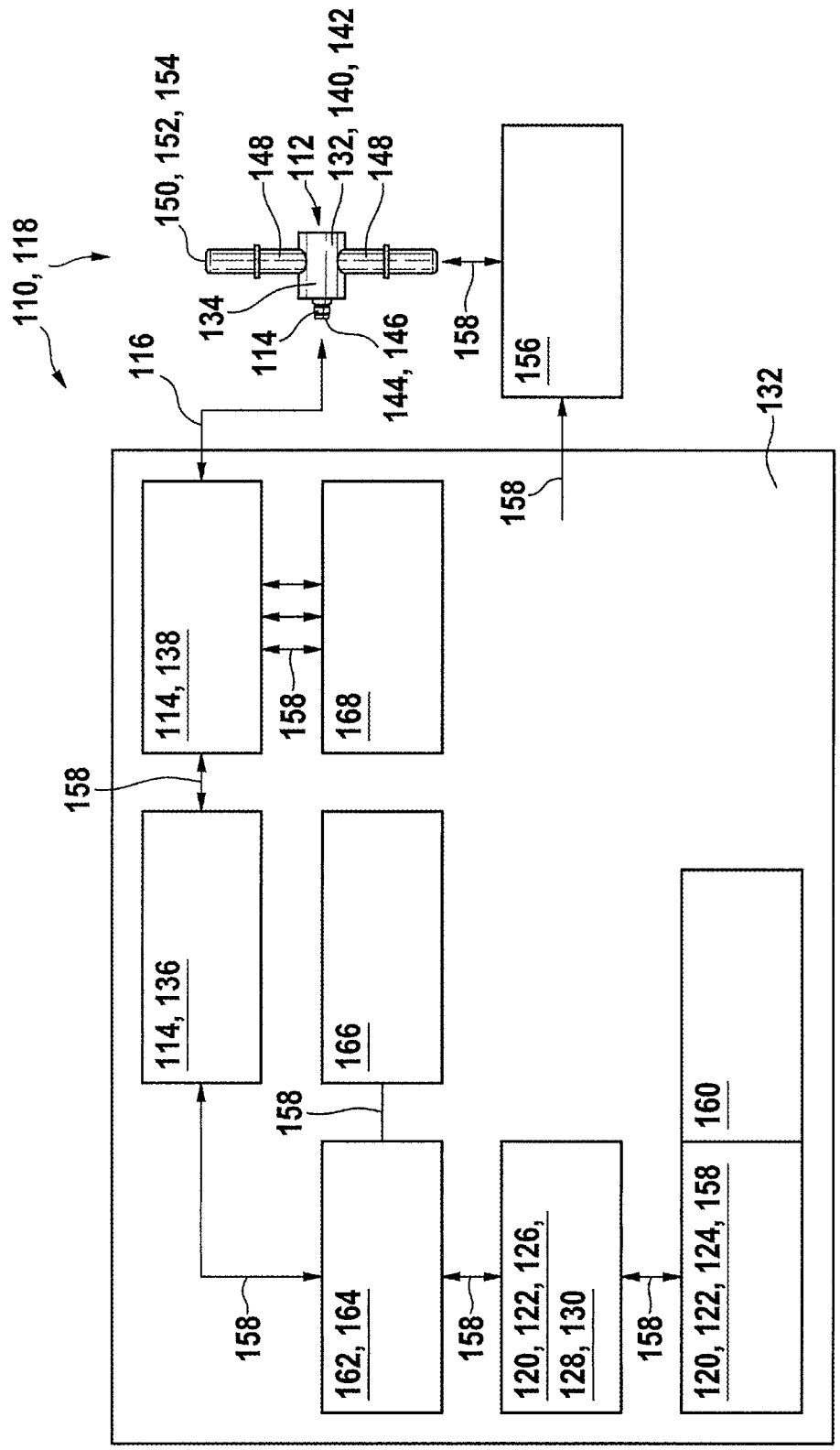
FIG. 2 shows a block diagram with a partial view of a further exemplary embodiment of a device according to the present invention for determining a composition of a liquid, especially of a fuel mixture, for use in motor vehicles.

FIGS. 1 and 2 show exemplary embodiments of a device 110 according to the present invention for determining a composition of a liquid, especially of a fuel mixture, for use in motor vehicles. It may be used in particular for determining at least a content of at least one component in the liquid, especially the fuel mixture. As shown in FIGS. 1 and 2, device 110 has at least one sensor 112. For example, sensor 112 may be implemented as described in DE 10 2008 044 383 A1 or the post-published DE 10 2010 029 007. In principle, sensor 112 may be implemented in any way desired. Sensor 112 has at least one connecting device 114 for coupling microwave signals 116 into the liquid, especially into the fuel mixture, and/or out of the liquid, especially out of the fuel mixture. Device 110 is in the form of a hand-held measuring instrument 118 as depicted in FIG. 1, for example.

In particular, device 110 may take the form of a fuel-quality measuring instrument as illustrated in FIG. 1. In particular, FIG. 2 shows components of the fuel measuring instrument, especially of device 110 according to the present invention.

Furthermore, device 110 may have at least one indicating unit 120 and/or operating unit 122, connectable, especially reversibly connectable, to sensor 112, particularly for displaying the composition and/or a case of a fault. Indicating unit 120 and/or operating unit 122 may include at least one display 124, e.g., a display 124 to display the component, especially to display the composition of the liquid, particularly of the fuel mixture, e.g., to display the content of the at least one component in the liquid, especially in the fuel mixture. Indicating unit 120 is able to display information, for example, and/or signals in case of a fault. For instance, indicating unit 120 may output signals, especially in the case of a fault, selected, illustratively, from the group made up of: "no filling"; "unknown mixture" and/or other signals. Unknown mixtures, e.g., liquids for use in motor vehicles, especially fuel mixtures, for which device 110 is completely or partly unable to determine the composition, may be filed in at least one memory 126, for example, depending on the embodiment variant. In particular, characteristic measuring results of the unknown mixture, e.g., resonant frequencies and/or at least one spectrum, may be filed and/or stored in memory 126. Unknown mixtures, e.g., liquids for use in motor vehicles, especially fuel mixtures, may thereby be recognized, for example. Furthermore, for example, a fuel value of the liquid, e.g., of the mixture, especially of the fuel mixture, may be calculated as weighted sum of the fuel values of the individual components, especially of the components, and/or displayed, particularly on indicating unit 120.

Device 110, particularly indicating unit 120 and/or operating unit 122, may include at least one data-processing device 128, especially at least one microcontroller 130. Data-processing device 128 and/or microcontroller 130 may have at least one evaluation software, for example, especially for evaluating the measuring results of sensor 112 and/or for calculations, e.g., to calculate the fuel value of the mixture as weighted sum of the fuel values of the individual components and/or to calculate the composition of the liquid, especially of the fuel mixture, e.g., to calculate the content of the component in the liquid, particularly in the fuel mixture. An evaluation in data-processing device 128 and/or in microcontroller 130 may be obtained in particular by an evaluation of the substance contents in the mixture, especially the composition of the liquid, particularly of the fuel mixture. Microcontroller 130 and/or data-processing device 128 may include, in particular, memory 126 and/or indicating unit 120 and/or operating unit 122 and/or be connected, especially connected electronically, to them at least in part. Data-processing device 128 and/or microcontroller 130 may, in particular, include at least one sequencing control, e.g., a sequencing control for measuring the measuring results and/or at least for performing at least one calibration, particularly to calibrate device 110. Microcontroller (μC) 130 and/or data-processing device 128 may be set up in particular to carry out a preprocessing (PP), illustratively, a determination of signal parameters, e.g., a determination of a transmission of microwaves and/or at least one amplitude and/or at least one frequency and/or at least one frequency spectrum. In addition, data-processing device 128 and/or microcontroller 130 may generate an input and/or output, e.g., by way of indicating unit 120 and/or operating unit 122.

Sensor 112 and/or device 110 may have at least one housing 132. In particular, at least one measuring area 134 may be accommodated in housing 132, especially in a housing 132 of sensor 112. The liquid, especially the fuel mixture, may be able to be introduced into measuring area 134. Connecting device 114 may be disposed at least partially in measuring area 134.

Connecting device 114 may, for example, have at least one transceiver coupler 136 and/or at least one selector switch 138, particularly for switching between the coupling of microwave signals 116 into the liquid, especially into the fuel mixture, and the coupling of microwave signals 116 into a calibration reference (Cal-Reference) 168.

Housing 132 may be made at least partially of at least one plastic suitable for fuel and/or a plastic impervious to fuel. For example, measuring area 134 may be traversable by the liquid, particularly the fuel mixture. Housing 132, especially housing 132 of sensor 112, may have at least one electrically conductive housing element 140 traversable by the liquid, particularly the fuel mixture. At least one inner conductor, which is covered by housing element 140 in the perspective representations of sensor 112 in FIGS. 1 and 2, may be introduced into housing element 140. The inner conductor may be surrounded at least partially, completely in FIGS. 2 and 1, by housing element 140.

Figure 3:
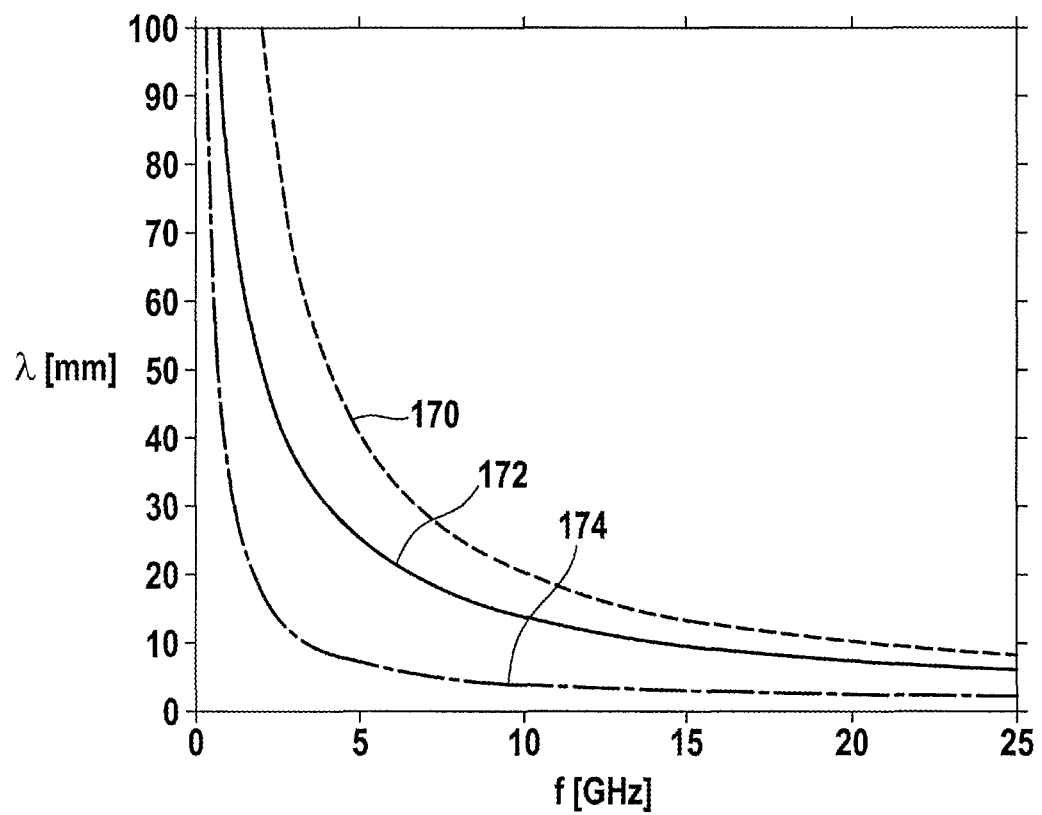
FIG. 3 shows a schematic representation of the dependency of the wavelength on the frequency for fossil fuel, ethanol and water.

Housing element 140 may enclose the inner conductor coaxially. Housing element 140 may have at least one cup 142 at least partially surrounding the inner conductor. Cup 142 may be connected electroconductively to the inner conductor. Cup 142 may have a plurality of boreholes; the boreholes may preferably have a diameter which is smaller than the smallest wavelength of the coupled-in microwaves, especially less than 2 mm, preferably less than 1 mm. FIG. 3 shows a schematic representation of the dependency of wavelengths λ in mm on frequencies f in GHz for various components of fuel mixtures and/or liquids, e.g., of flex fuel contents, especially of fossil fuel (broken line 170), ethanol (solid line 172) and water (dot-dash line 174), the wavelengths and frequencies being able to be used, for example, in device 110 of the present invention. For example, for E100, thus fuel, especially a fuel mixture, having a nominal ethanol content of 100%, given a frequency f=19 GHz, the wavelength, particularly because of the dispersive properties of the ethanol, is usually approximately λ=7 mm. Connecting device 114 may have at least one coaxial connector 144. Coaxial connector 144 may include at least one contact 146 for applying microwave signals 116 to connecting device 114, especially the inner conductor.

Device 110, particularly sensor 112 and/or housing 132 and/or housing element 140 and/or housing 132 of sensor 112 may furthermore have at least one flow-pipe section 148 traversable by the liquid, particularly the fuel mixture, in a direction of flow. The inner conductor and housing element 140 may be introduced transversely, preferably essentially perpendicular, to the direction of flow in flow-pipe section 148. Device 110, especially sensor 112, may in particular include at least one plug-in cartridge, the plug-in cartridge encompassing the inner conductor and/or housing element 140. The plug-in cartridge may be plugged into an accommodation of flow-pipe section 148 in measuring area 134 transversely to the direction of flow. The plug-in cartridge may be sealed off with respect to flow-pipe section 148 by at least one sealing element. Housing element 140 and/or the inner conductor may be accommodated in measuring area 134. A flow-pipe cross-section may be expanded in measuring area 134 compared to a flow-pipe cross-section outside of measuring area 134.

Sensor 112 and/or device 110 may include at least one sensor head 150. Sensor head 150 may include at least one admission device 152 for admitting the liquid, particularly the fuel mixture, to sensor 112. Sensor head 150 may, in particular, include at least one admission device 152 selected from the group made up of a funnel device and an adapter 154, particularly an adapter 154 for the connection of a quick hose connector. Sensor 112 and/or sensor head 150 may be completely or partially immersible in the liquid, particularly in the fuel mixture, especially in a tank containing the liquid, particularly the fuel mixture. For example, the funnel may be a funnel device for filling sensor 112. Alternatively or additionally, sensor 112 and/or sensor head 150 may also be a sensor 112 for dipping into the fuel, e.g., into the liquid, especially into the fuel mixture. Moreover, alternatively or additionally, there is the possibility, e.g., to connect a quick hose connector to adapter 154, for instance.

All components of device 110 which could come in contact with the liquid, particularly the fuel mixture, are preferably made of a material suitable for use with fuel and/or impervious to fuel, e.g., a plastic suitable for and/or impervious to fuel and/or a fuel-suitable and/or fuel-impervious metal and/or a fuel-suitable and/or a fuel-impervious ceramic material. Thus, depending on the exemplary embodiment, device 110, particularly hand-held measuring instrument 118 and/or sensor head 150 and/or sensor 112 may be filled with the liquid, e.g., the fuel, especially the fuel mixture and/or may be dipped into the liquid, e.g., into the fuel, especially into the fuel mixture.

Device 110, particularly sensor 112, may include at least one temperature sensor 156. Temperature sensor 156 may be designed in particular to detect an outside temperature and/or a temperature of the liquid, especially of the fuel mixture. Temperature sensor 156 may be integrated into sensor head 150 and/or into housing 132 and/or into sensor 112, however may also be completely or partially separate from these components. For example, temperature sensor 156 may be connected to housing 132, especially to data-processing device 128 and/or to microcontroller 130 and/or to indicating unit 120 and/or to operating unit 122 in such a way that information is able to be transmitted from temperature sensor 156 to the respective components, e.g., data-processing device 128, and/or information is able to be transmitted from the indicated components to temperature sensor 156. In particular, temperature sensor 156 may be connected to sensor head 150 and/or sensor 112 and/or housing 132 via at least one, preferably two interfaces 158.

Thus, device 110, particularly hand-held measuring instrument 118, may, for example, include one or more of the following components and/or of the previously indicated components: sensor 112, e.g., as described in the post-published DE 10 2010 029 007 or in DE 10 2008 044 383 A1, for example, having the at least one temperature sensor 156; microcontroller 130 having the evaluation software; display 124 for the display of the components, especially the components of the liquid, particularly the components of the fuel mixture; the at least one funnel device; the at least one indicating unit 120 and/or the at least one operating unit 122; sensor head 150, e.g., for a quick hose connector and/or for immersion; at least one interface 158, including, for example, at least one CAN (Controller Area Network) and/or an interface device for generating a PWM (pulse width modulation) signal and/or at least one serial interface device, e.g., at least one Universal Serial Box (USB) for the connection of at least one personal computer (PC) and/or at least one data logger; at least one current supply and/or at least one voltage supply, e.g., an automotive DC supply 160; at least one radio chip, e.g., at least one HF-ASIC 162 and/or at least one ASIC 164; at least one HF peripheral 166; at least one calibration reference (Cal-Reference) 168, e.g., including at least one memory 126 and/or at least one reference, for example, a reference termination, e.g., a short circuit and/or a no-load operation and/or a non-reflecting termination; transceiver coupler 136; selector switch 138; sensor 112. The components indicated may be at least partially separate and/or may be connected at least partially to one another. For example, as shown in FIG. 2, automotive DC supply 160 may be implemented at least partially together with interface 158, especially the CAN and PWM. For instance, they may be connected at least in part to microcontroller 130. Microcontroller 130 may be connected at least in part to HF-ASIC 162. HF-ASIC 162 may be connected at least partially, for instance, to transceiver coupler 136. Transceiver coupler 136 may be connected at least in part to selector switch 138, for example. Selector switch 138 may be connected at least partially to sensor 112. Sensor 112 may be connected at least in part to temperature sensor 156. For example, "be connected" may be understood to mean that information, e.g., electrical signals and/or microwave signals 116 and/or other information, may be exchanged between the respective components. For instance, "be connected" may allude to the presence of a mechanical and/or electromagnetic connection, e.g., by at least one interface 158. Furthermore, HF-peripheral 166 may be connected at least partially to HF-ASIC 162. Cal-reference 168 may be connected at least in part to selector switch 138, for example, may also be connected several times, e.g., by at least one, preferably three interfaces 158. As shown in FIGS. 1 and 2, sensor 112 may be disposed outside of a housing 132, which preferably may contain at least a portion of the remaining components of device 110 of the present invention indicated above.

For example, device 110 may take the form of a built-in unit, e.g., for installation in a pump for pumping the liquid, especially for a blender pump. In this case, under the term built-in unit may be understood to be a property of device 110 which makes it possible to at least partially integrate and/or install, especially permanently install, device 110 in at least one other device. For instance, device 110 may include at least one interface and/or at least one fitting device, particularly at least one connection possibility, for example, at least one aperture, e.g., having a thread, and/or at least one holder and/or at least one bar and/or at least one possibility for a screw connection and/or welding and/or bonding and/or riveting. The built-in unit may be set up to be integrated and/or installed at least permanently to some extent or reversibly in at least one other device, e.g., in the blender pump and/or in the motor vehicle. A blender pump may be understood to be a device which may be used for withdrawal and/or mixing of the liquid, especially the fuel mixture. For example, the blender pump may be in the form of a fuel pump, especially for the withdrawal and/or mixing of a fuel mixture preselected by the user, particularly with preselected composition of the fuel mixture or the liquid.

For instance, sensor 112 may be reversibly exchangeable, various types of sensors 112 being able to be used, particularly in order to employ device 110 for various types of liquids and/or fuel mixtures like those listed above, for example. Sensor 112 may be selected from the group made up of: a biodiesel-fuel sensor; a urea/water solution sensor; an alcohol solution sensor; an antifreeze/coolant sensor. The exchange and/or the use of other sensors 112, e.g., for other liquids, especially for other fuel mixtures, may also be possible in principle. For example, the biodiesel-fuel sensor may be a sensor 112 designed to determine an ethanol content and/or a water content and/or a fossil content and/or a lead content and/or a sulfur content and/or a further content in a fuel mixture, especially in a biodiesel fuel. The urea/water solution sensor may be a sensor 112, for example, which is designed to determine a urea content and/or a water content, e.g., in the urea/water solution. The alcohol solution sensor, for instance, may be a sensor 112 which is designed to determine an alcohol content, e.g., in the aqueous solution. The antifreeze/coolant sensor may, for instance, be a sensor 112 which is designed to determine an antifreeze content, e.g., in the coolant. For instance, sensor 112 may also be a combination of sensors 112 indicated, or, for example, one of sensors 112 indicated may be combined with at least one other or at least one similar sensor 112.

What is claimed is:

1. A determining device for determining at least one component of a liquid, comprising:
   at least one sensor determining the at least one component, wherein the sensor has at least one connecting device for coupling microwave signals at least one of into the liquid or out of the liquid;
   wherein the determining device is configured as a hand-held measuring instrument,
   wherein the sensor includes:
      at least one sensor head, and
      at least one flow-pipe section through which the liquid flows, the at least one flow-pipe section extending at least essentially transversely to an axis of the at least one connecting device,
   wherein the sensor head includes at least one admission device for admitting the liquid to the sensor, wherein the at least one admission device is of one of a funnel device and an adapter for connection of a quick hose connector, wherein the at least one admission device is disposed at an end of the at least one flow-pipe section.

2. The device as recited in claim 1, further comprising:
   at least one of an indicating unit or an operating unit detachably connected to the sensor and configured to display at least one of (i) the at least one component or (ii) a fault condition.

3. The device as recited in claim 2, wherein the at least one of the indicating unit or the operating unit includes at least one display.

4. The device as recited in claim 3, wherein the at least one of the indicating unit or the operating unit includes at least one microcontroller.

5. The device as recited in claim 4, wherein the sensor has at least one housing which accommodates at least one measuring area into which the liquid is introduced, and wherein the connecting device is disposed at least partially in the measuring area.

6. The device as recited in claim 1, wherein the sensor is one of a biodiesel-fuel sensor, a urea/water solution sensor, an alcohol solution sensor, and an antifreeze/coolant sensor.

7. The device as recited in claim 1, wherein the determining device is configured as a built-in unit for a blender pump.

* * * * *